United States Patent [19]
Kai et al.

[11] Patent Number: 5,604,032
[45] Date of Patent: Feb. 18, 1997

[54] FLUORINE-CONTAINING CARBOXYLIC ACID AMINE SALT AND A MAGNETIC RECORDING MEDIUM WITH THE SAME THEREON

[75] Inventors: Yoshiaki Kai, Neyagawa; Yukikazu Ohchi, Osaka, both of Japan

[73] Assignee: Matsushita Electric Industrial Co., Ltd., Osaka, Japan

[21] Appl. No.: 322,551

[22] Filed: Oct. 13, 1994

[30] Foreign Application Priority Data

Oct. 19, 1993 [JP] Japan .................................. 5-260757

[51] Int. Cl.$^6$ ......................................... G11B 5/71
[52] U.S. Cl. .................. 428/336; 428/341; 428/421; 428/694 TC; 428/694 TF; 428/694 TB; 428/900; 560/197; 562/606; 508/478; 508/496; 508/497
[58] Field of Search ...................... 560/197; 428/694 TC, 428/694 TF, 694 TB, 341, 421, 336, 900; 252/51.5; 562/606

[56] References Cited

U.S. PATENT DOCUMENTS

| | | | |
|---|---|---|---|
| 5,091,269 | 2/1992 | Kondo et al. | 428/695 |
| 5,128,216 | 7/1992 | Ng | 428/695 |
| 5,188,747 | 2/1993 | Kai et al. | 252/54 |
| 5,391,814 | 2/1995 | Kai et al. | 560/197 |

FOREIGN PATENT DOCUMENTS

| | | |
|---|---|---|
| 0473871A3 | 3/1992 | European Pat. Off. . |
| 4-274018 | 9/1992 | Japan . |

OTHER PUBLICATIONS

Patent Abstracts of Japan, vol. 18, No. 624 (P–1833) & JP–A–62 036545 (Matsushita Electric Ind.), abstract only Nov. 1994.

Database WPI, Week 9403, Derwent Publications Ltd., London, GB; AN 94–023122 & JP–A–05 331 473 (Sony), abstract only Dec. 1993.

Database WPI, Week 9415, Derwent Publications Ltd., London, GB, AN 94–121664 & JP–A–06 068 455 (Sony), abstract only Mar. 1994.

*Primary Examiner*—Stevan A. Resan
*Attorney, Agent, or Firm*—Fish & Richardson P.C.

[57] ABSTRACT

A fluorine-containing carboxylic acid amine salt of Formula A below:

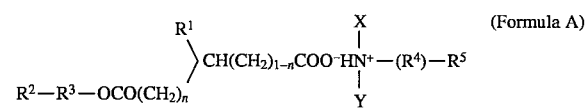

wherein $R^1$ denotes an aliphatic alkyl group or an aliphatic alkenyl group with 6 to 30 carbons; $R^2$ denotes a group selected from the group consisting of a fluoroalkyl group with 3 to 30 carbons, a fluoroalkenyl group with 3 to 30 carbons, a fluorophenyl group with 6 to 18 carbons, and a fluoroalkylether group with 5 to 50 carbons; $R^3$ and $R^4$ each denotes a saturated or unsaturated hydrocarbon chain with 1 to 20 carbons; $R^5$ denotes either a fluoroalkyl group with 3 to 30 carbons or a fluoroalkenyl group with 3 to 30 carbons; n denotes 0 or 1; X denotes hydrogen or -($R^6$)-$R^7$; and Y denotes hydrogen or -($R^8$)-$R^9$, where $R^6$ and $R^8$ each denotes a saturated or unsaturated hydrocarbon chain with 1 to 20 carbons, and $R^7$ and $R^9$ each denotes a fluoroalkyl group with 3 to 30 carbons or a fluoroalkenyl group with 3 to 30 carbons.

13 Claims, 4 Drawing Sheets

FLUORINE-CONTAINING CARBOXYLIC ACID AMINE SALT AND A MAGNETIC RECORDING MEDIUM WITH THE SAME THEREON

FIELD OF THE INVENTION

This invention relates to a fluorine-containing carboxylic acid amine salt which can be used for lubricants of precision machinery and precision parts in which highly accurate lubricity is required, a surface active agent, a mold releasing agent, and an anticorrosive agent or the like. This invention further relates to a magnetic recording medium with the fluorine-containing carboxylic acid amine salt thereon.

BACKGROUND OF THE INVENTION

Along with the advancement toward small-sized and highly accurate machinery devices and machinery parts, the lubrication used with sliding members is changing from fluid lubrication to boundary lubrication. Particularly, in the field of electronics and electronic parts such as a VTR or a magnetic disk, the use of a ferromagnetic metallic thin film with the intention of improving memory density requires highly accurate lubrication for sliding a magnetic recording medium on a magnetic head. For example, an evaporation tape and a hard disk are designed to achieve a higher output by minimizing the spacing between a magnetic recording medium and a magnetic head without losing durability and reliability. Therefore, a lubricant layer disposed on the surface of a magnetic layer is formed such that the thickness is only several nm (10 angstroms). Thus, an organic compound with high lubricity which is used to form this lubricant layer has become the major task of development.

As lubricants for metallic thin film type magnetic recording mediums, a long-chain carboxylic acid perfluoroalkyl amine salt shown in Formula 1 below, an aliphatic carboxylic acid with a fluoroalkylether group shown in Formula 2 below, and an aliphatic carboxylic acid with a fluoroalkyl group shown in Formula 3 below are disclosed due to their compatibility with metallic thin films (Laid-open Japanese Patent Application Nos. Hei 4-274018 and Hei 4-270243).

$$C_{18}H_{37}COO^-H_3N^+(CH_2)_{10}C_8F_{17} \quad \text{(Formula 1)}$$

(Formula 2)

(Formula 3)

However, the lubricants shown in the above-noted Formulas 1, 2 or 3 were transferred onto a backing side when magnetic tapes were stored in an environment of high temperature and high humidity. The problem was that the lubricity deteriorated because the amount of lubricant present on the surface of the magnetic layer decreased through this transfer. This deterioration of lubricity becomes even more obvious as it results in lower steel endurance.

SUMMARY OF THE INVENTION

It is an object of this invention to solve the above-mentioned conventional problems by providing a material which can maintain lubricity even after being stored in an environment with high temperature and high humidity. Another object of this invention is to provide a magnetic recording medium having the above-mentioned material on the surface.

These and other objects and advantages of the invention are accomplished with the fluorine-containing carboxylic acid amine salt shown in the formula below:

(Formula 4)

wherein $R^1$ denotes an aliphatic alkyl group or an aliphatic alkenyl group with 6 to 30 carbons; $R^2$ denotes a group selected from the group consisting of a fluoroalkyl group with 3 to 30 carbons, a fluoroalkenyl group with 3 to 30 carbons, a fluorophenyl group with 6 to 18 carbons, and a fluoroalkylether group with 5 to 50 carbons; $R^3$ and $R^4$ each denotes a saturated or unsaturated hydrocarbon chain with 1 to 20 carbons; $R^5$ denotes a fluoroalkyl group with 3 to 30 carbons or a fluoroalkenyl group with 3 to 30 carbons; n denotes 0 or 1; X denotes hydrogen or $-(R^6)-R^7$; and Y denotes hydrogen or $-(R^8)-R^9$, where $R^6$ and $R^8$ each denotes a saturated or unsaturated hydrocarbon chain with 1 to 20 carbons, and $R^7$ and $R^9$ each denotes a fluoroalkyl group with 3 to 30 carbons or a fluoroalkenyl group with 3 to 30 carbons.

It is preferable in the above-noted Formula 4 that $R^1$ is an aliphatic alkyl group or an aliphatic alkenyl group with 10 to 24 carbons; $R^2$ is selected from the group consisting of a fluoroalkyl group with 6 to 18 carbons, a fluoroalkenyl group with 3 to 30 carbons, a fluorophenyl group with 6 to 12 carbons, and a fluoroalkylether group with 5 to 30 carbons; $R^3$ and $R^4$ each is a saturated or unsaturated hydrocarbon chain with 1 to 10 carbons; $R^5$ is a fluoroalkyl group with 6 to 18 carbons or a fluoroalkenyl group with 6 to 18 carbons; $R^6$ and $R^8$ each is a saturated or unsaturated hydrocarbon chain with 1 to 10 carbons; and $R^7$ and $R^9$ each is a fluoroalkyl group with 6 to 18 carbons or a fluoroalkenyl group with 6 to 18 carbons.

Next, a magnetic recording medium of this invention comprises a base material film disposed thereon with a ferromagnetic film and a lubricant layer containing a lubricant disposed either directly or via a protection film on top of said ferromagnetic film, wherein said lubricant layer contains the fluorine-containing carboxylic acid amine salt shown in the above-noted Formula 4.

It is preferable that the lubricant of Formula 4 is present in the lubricant layer in an amount of from 0.05 to 100 mg per 1 $m^2$ film surface.

It is also preferable that the lubricant contained in the lubricant layer comprises fluorine-containing carboxylic acid amine salt of Formula 4 at 90 weight percent or more.

Furthermore, it is preferable that the lubricant contained in the lubricant layer comprises 50 weight percent or more of the fluorine-containing carboxylic acid amine salt shown in Formula 4 and also a lubricant and an anticorrosive agent, preferably made of other fluorine-containing compounds. Examples of other fluorine-containing compounds are $C_{17}H_{33}COOC_2H_4C_6F_{13}$ as a lubricant and $C_8F_{17}C_2H_4NHC_{18}H_{35}$ as an anticorrosive agent.

In addition, it is preferable that the lubricant and anticorrosive agents made of other fluorine-containing compounds are liquid fluorine-containing compound. Examples of the liquid fluorine-containing compound are the compound shown in Example 5 and compounds shown in Example 6 (Formulas 11 to 15).

It is preferable that the protection film has a thickness of from 5 to 50 nm and is at least one film selected from the group consisting of an amorphous-form carbon thin film, a graphite-form carbon thin film, a diamond-form carbon thin film, a mixed-form carbon thin film thereof, and a laminated-form carbon thin film thereof.

It is also preferable that the base material film has a thickness of from 3 to 30 μm and is at least one film selected from the group consisting of polyethylene terephthalate, polyethylene 2,6-naphthalate, and polyimide.

Furthermore, it is preferable that the ferromagnetic film is a Co—Ni—O-type alloyed oxide film and has a thickness of from 80 to 300 nm (800 to 3000 angstroms).

It is preferable that the base material film is disposed with a backing layer on the back side.

In addition, it is preferable that the backing layer is a compound containing a binder resin and a filler material.

It is also preferable that the binder resin is at least one resin selected from the group consisting of polyester elastomer and cellulose nitrate, and said filler material is at least one material selected from the group consisting of calcium carbonate and carbon black.

Referring to the above-noted formula (Formula 4), it is preferable that $R^1$ comprises 6 to 30 carbons, more preferably 10 to 24 carbons, since the lubricity tends to deteriorate when the number of carbons becomes less than 6 or more than 30. $R^2$ preferably contains 3 to 30 carbons and more preferably 6 to 18 fluoroalkyl or 6 to 18 fluoroalkenyl groups which may have ether or ether with phenyl as a bonding group. $R^2$ preferably contains 6 to 18 carbons and more preferably 6 to 12 fluorophenyl groups. $R^2$ preferably contains 5 to 50 carbons or more preferably 5 to 30 fluoroalkylether groups. When the number of carbons goes beyond these limits, either lubricity or storage reliability tends to deteriorate. It is preferable that $R^3$ and $R^4$ each has 1 to 20 carbons, more preferably 1 to 10 carbons as either a saturated or unsaturated hydrocarbon chain. When the number of carbons goes beyond 20, either lubricity or storage reliability tends to deteriorate. It is preferable that $R^5$ has 3 to 30 carbons and more preferably 6 to 18 fluoroalkyl groups or fluoroalkenyl groups and ether or ether with phenyl as a bonding group. The storage reliability tends to deteriorate when the number of carbons is beyond these limits.

A magnetic recording medium of this invention comprises a base material film disposed thereon with a ferromagnetic film and a lubricant layer disposed either directly or via a protection film on top of the ferromagnetic film, in which the lubricant layer contains one or more kinds of fluorine-containing carboxylic acid amine salt of Formula 4.

This lubricant layer is present in the form of a thin layer comprising the fluorine-containing carboxylic acid amine salt solely or including other lubricants and anticorrosive agents. The lubricant contained in the lubricant layer is preferably present in an amount of from 0.05 to 100 mg and more preferably from 0.1 to 50 mg per 1 m² film surface. Suitable other lubricants and anticorrosive agents mentioned above include fluorine-containing compounds or more preferably liquid fluorine-containing compounds. These additives are preferably present in an amount of from 1 to 80 weight percent or more preferably 0 to 70 weight %. It is more difficult to attain the effect of this invention when the fluorine-containing carboxylic acid amine salt of Formula 4 is present in an amount of less than 20 weight %.

It is preferable that the protection film is a carbon thin film of an amorphous form, a graphite form, a diamond form, a mixed form thereof, and a laminated form thereof which can be obtained by using a method such as a sputtering, plasma CVD or the like. It is preferable that the thickness is from 5 to 50 nm (50 to 500 angstroms).

A fluorine-containing carboxylic acid amine salt of this invention comprises two fluorine-containing hydrocarbon end groups within the same molecule, i.e., fluoroalkyl end groups, fluoroalkenyl end groups, fluorophenyl end groups or fluoroalkylether end groups, one aliphatic hydrocarbon end group, i.e., an aliphatic alkyl end group or an aliphatic alkenyl end group, and an amine carboxyl group. Since the fluorine-containing hydrocarbon end group has a lipophobic property, the affinity is poor with a backing layer comprising a hydrocarbon polymer. On the other hand, the aliphatic hydrocarbon end group having a liphophilic property has excellent affinity with a backing layer. However, when more fluorine-containing hydrocarbon end groups are present than aliphatic hydrocarbon end groups within the same molecule, the molecule has a strong lipophobic property as a whole so that the affinity with the backing layer becomes weak. Therefore, the fluorine-containing carboxylic acid amine salt can be controlled from transferring itself to the backing layer, in other words, from reducing its amount on the magnetic layer surface, so that a magnetic tape does not suffer degradation over time.

An amine carboxyl group adheres strongly to either a surface of a metallic thin film or of a protection film and also to a surface of a magnetic head. Furthermore, the fluorine-containing hydrocarbon end group is exposed on a surface, thereby contributing to reduction of energy on the surface and forming a non-adhesive face. In addition, an aliphatic hydrocarbon end group forms a flexible carbon—carbon bonding chain so that it shows good lubricity. Accordingly, through a multiplier effect of each of these end groups, the fluorine-containing carboxylic acid amine salt of this invention can demonstrate excellent lubricity in any condition such as from a low humid environment (e.g., 5° C., 5% RH) to a high humid environment (e.g., 40° C., 80% RH).

DETAILED DESCRIPTION OF THE INVENTION

EXAMPLE 1

A first embodiment of this invention is specifically described in the following illustrative example. The material of this embodiment is shown in Formula 5:

(Formula 5)

(molecular weight 1,603)

The above-mentioned material is within the scope of Formula 4 mentioned above where $R^1$ designates an aliphatic alkyl group with 18 carbons; $R^2$, a fluoroalkylether group with 11 carbons bonded to fluorines; $R^3$, a hydrocarbon chain with one carbon; $R^4$, a saturated hydrocarbon chain with 10 carbons; $R^5$, a fluoroalkenyl group comprising 9 carbons bonded to fluorine and ether as a bonding group; and n is 1.

Next, a manufacturing method of the material shown in the above-noted Formula 5 is described hereafter.

A starting material is an amine with a fluoroalkenyl group shown in Formula 6 and a material shown in Formula 7.

$$C_9F_{17}O(CH_2)_{10}NH_2 \qquad \text{(Formula 6)}$$

(Formula 7)

The material shown in Formula 7 is a composite of stearic succinic anhydride and 1H, 1H-perfluoro-2,5,8-trimethyl-3,6,9-trioxaundecane-1-ol. 100.0 g (0.10 mol) of the material shown in Formula 7 and 1000 ml of ethyl acetate were extracted into a 2-liter-flask with mixing wings, cooled to a temperature of 15° C., and dripped with 66.4 g (0.11 mol) of the material shown in Formula 6 which was dissolved in 400 ml of ethyl acetate. When the dripping was over, the reactive solution was put back at room temperature and was stirred continuously for two hours. After the reaction took place, the reactive solution was cooled to 0° C., and the reactive product was recrystallized. Then, an unreacted amine with a fluoroalkenyl group was eliminated by a filtration under reduced pressure, thereby obtaining 115 g of white solid whose fusion point was 72° C. This white solid underwent an infrared spectroscopic analysis (IR), a gel permeation chromatography (GPC) and an organic mass spectrometry (FD-MS) and was identified as the fluorine-containing carboxylic acid amine salt shown in Formula 5 which contained neither the starting material nor a by-product.

Figure 3:
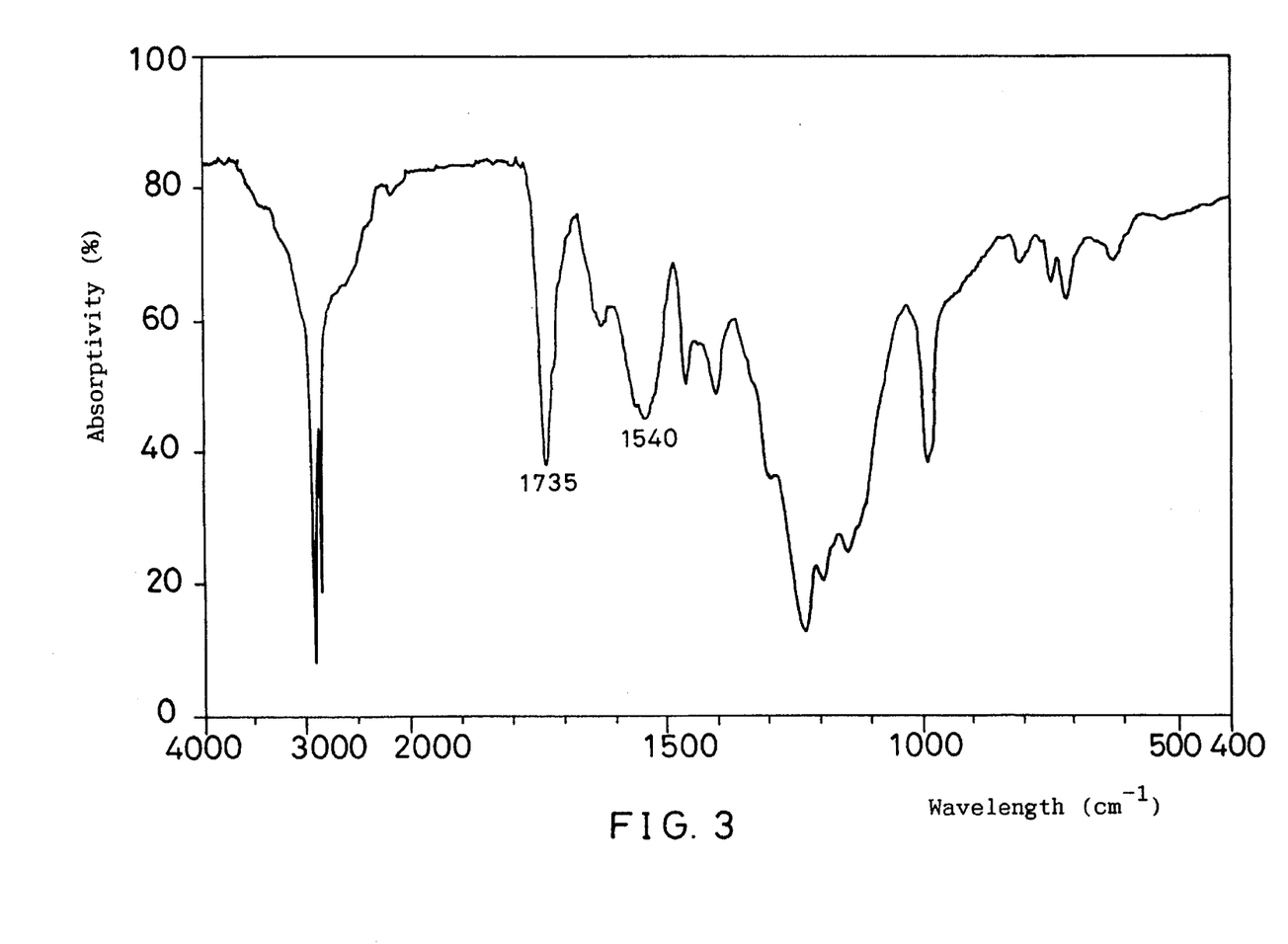
FIG. 3 is an infrared ray (IR) spectral chart of a first embodiment of this invention.

IR; an absorption peak of carboxylic acid disappeared at 1,705 cm$^{-1}$, an absorbtion peak of carboxylic acid amine salt appeared at 1540 cm$^{-1}$ (FIG. 3).

GPC; the starting material and a by-product were not detected.

FD-MS; m/e a main peak was present at 1,603.

EXAMPLE 2

Next, a second embodiment of this invention is specifically described in the following illustrative example.

A material of this embodiment is shown in Formula 8:

(Formula 8)

(molecular weight 1,316)

The material in Formula 8 is within the scope of Formula 4 where $R^1$ designates an aliphatic alkenyl group with 18 carbons; $R^2$, a fluoroalkyl group with 6 carbons bonded to fluorine; $R^3$, an unsaturated hydrocarbon chain with 11 carbons; $R^4$, a saturated hydrocarbon chain with 3 carbons; $R^5$, a fluoroalkyl group with 8 carbons bonded to fluorine; and n is 1.

Next, the manufacturing method of the material shown in Formula 8 is explained hereafter.

The starting material is an amine with a fluoroalkyl group shown in Formula 9 and a material shown in Formula 10. The material shown in Formula 10 is a composite of 2-octa-desenyl succinic anhydride and 11-(perfluoro-n-hexyl)-10-undecanol (undecyl alcohol).

$$C_8F_{17}(CH_2)_3NH_2 \qquad \text{(Formula 9)}$$

(Formula 10)

83.9 g (0.10 mol) of the material shown in Formula 10 and 1000 ml of ethyl acetate were extracted into a 2-liter-flask with mixing wings, cooled to a temperature of 15° C., and dripped with 52.5 g (0.11 mol) of the material shown in Formula 9 which was dissolved in 400 ml of ethyl acetate. When the dripping was over, the reactive solution was put back at room temperature and was stirred continuously for two hours. After the reaction took place, the reactive solution was cooled to −20° C., and the reactive product was freezed and deposited. Then, an unreacted amine with a fluoroalkyl group was eliminated through a low temperature filtration, thereby obtaining 88 g of hyaline liquid. This hyaline liquid was analysed by IR, GPC and FD-MS and was identified as the fluorine-containing carboxylic acid amine salt shown in Formula 8 which contained neither the starting material nor a by-product.

Figure 4:
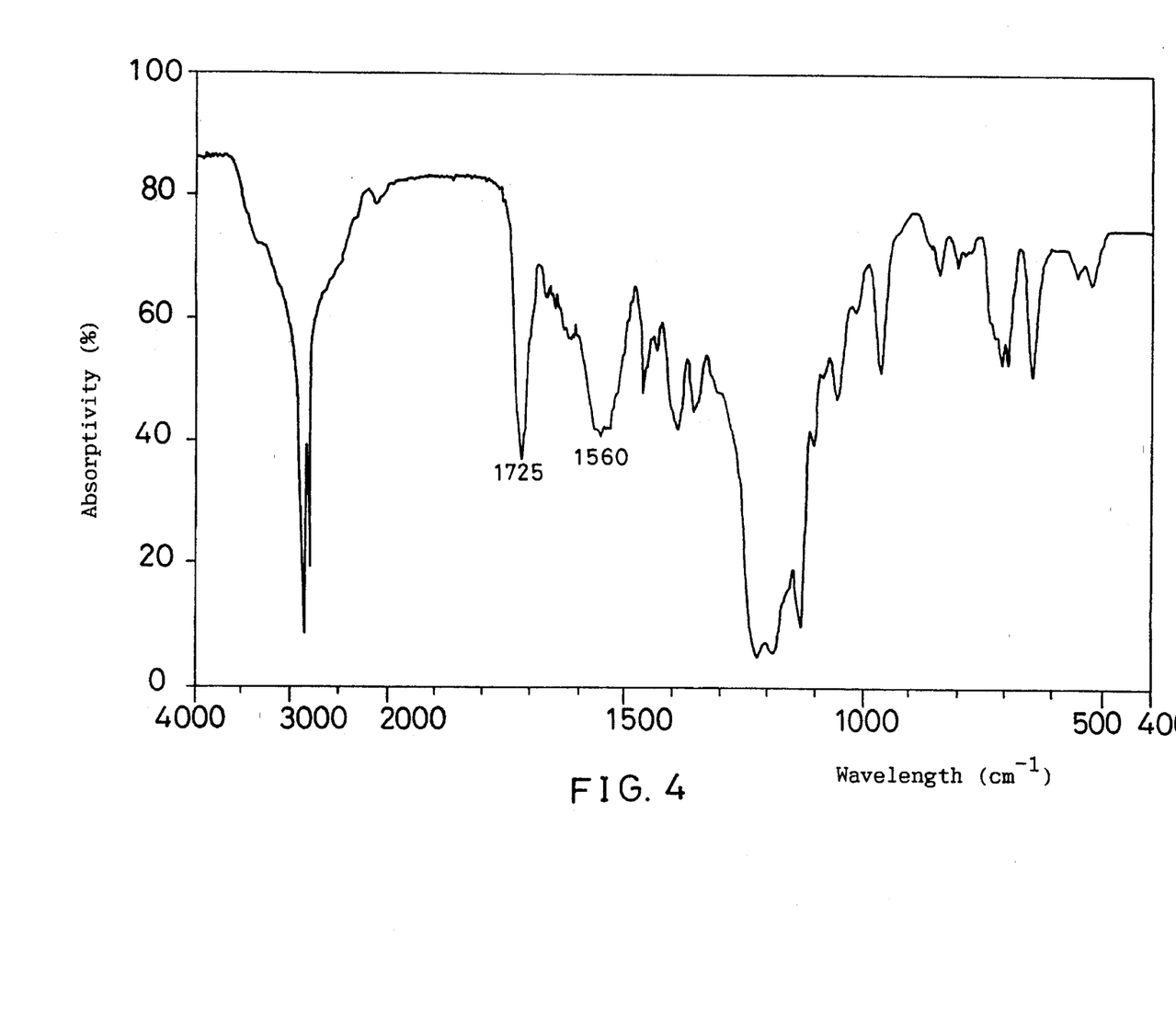
FIG. 4 is an infrared ray (IR) spectral chart of a second embodiment of this invention.

IR; an absorption peak of carboxylic acid disappeared at 1,705 cm$^{-1}$, an absorbtion peak of carboxylic acid amine salt appeared at 1540 cm$^{-1}$ (FIG. 4).

GPC; the starting material and a by-product were not detected.

FD-MS; m/e a main peak was present at 1,316.

EXAMPLE 3

Figure 1:
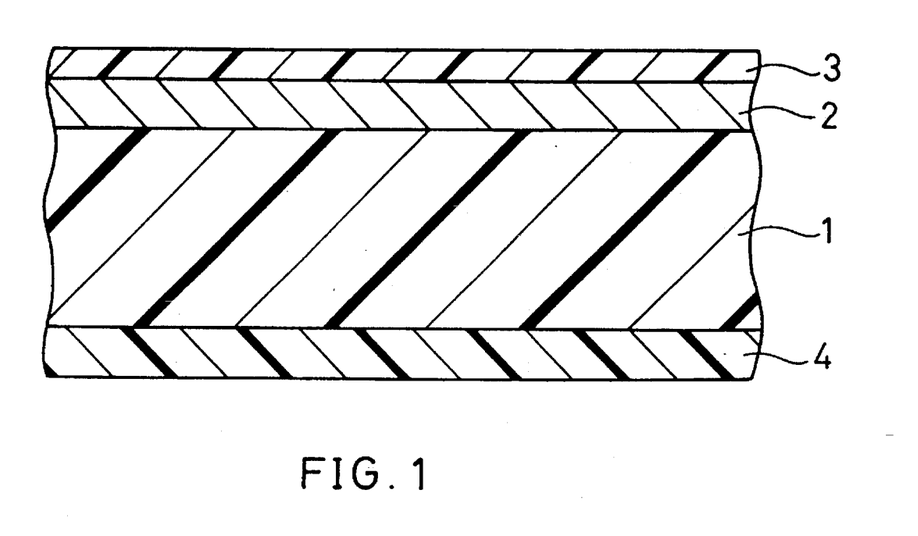
FIG. 1 is a cross-sectional view of a magnetic recording medium disposed with a lubricant comprising the fluorine-containing carboxylic acid amine salt in an embodiment of this invention.

Next, a magnetic recording medium of this invention is specifically described in the following illustrative example. FIG. 1 is a cross-sectional view of a magnetic recording medium in an embodiment of this invention. Referring to FIG. 1, reference numeral 1 denotes a base material film having a thickness of from 3 to 30 μm which is at least one film selected from the group consisting of polyethylene terephthalate, polyethylene 2, 6-naphthalate, and polyimide; 2, a ferromagnetic film such as a Co—Ni—O-type alloyed oxide film; 3, a lubricant layer formed of a fluorine-containing carboxylic acid amine salt of this invention; and 4, a backing layer. Backing layer 4 comprises, for example, 30 weight percent of polyester elastomer (polybutylene terephthalate—polytetrafluoroether copolymer) (BYRON manufactured by Toyobo Co., Ltd.), 20 weight percent of cellulose nitrate, 30 weight percent of calcium carbonate particulates, and 20 weight percent of carbon black. It is preferable that the backing layer has a thickness of from 3 to 10 μm and surface resistance of 10$^{10}$ ohm/cm$^2$ or less.

Figure 2:
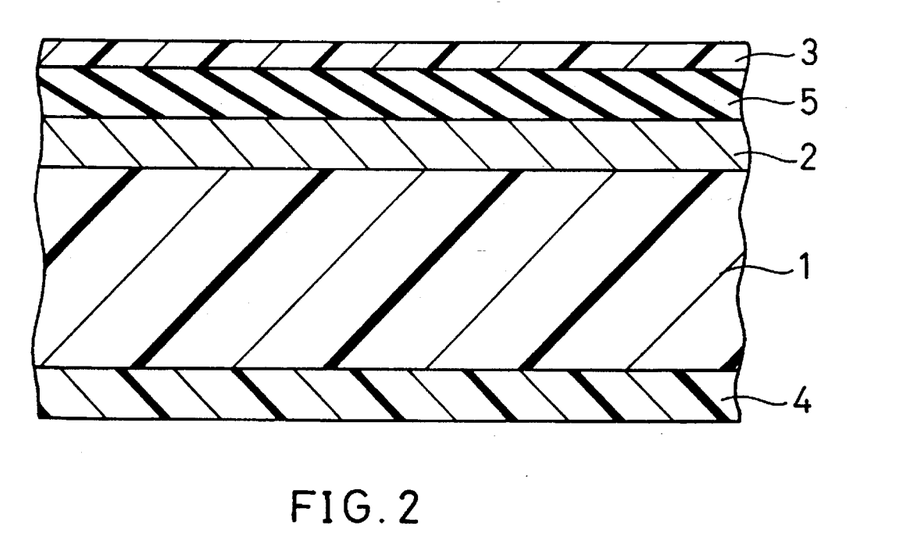
FIG. 2 is a cross-sectional view of a magnetic recording medium disposed with a lubricant comprising the fluorine-containing carboxylic acid amine salt in another embodiment of this invention.

FIG. 2 shows an embodiment in which a protective film 5 is disposed between a ferromagnetic film 2 and a lubricant layer 3. By disposing protective layer 5, ferromagnetic film 2 does not deteriorate through oxidation so that it can be used stably for a long period of time. In FIGS. 1 to 2, in order to enhance stickiness between base material film 1 and ferromagnetic film 2, an intermediate layer (not shown) may be disposed on the surface of base material film 1.

Embodiments will be specifically described in the following.

In a magnetic recording medium of this embodiment, base material film 1 comprises a polyester film which has several granular projections per surface of 100 $\mu m^2$ (average height: 7 nm (70 angstroms); diameter: 1 $\mu m$) with a gentle slope formed by silica particulates added within a polyethylene terephthalate film in which relatively large projections of particulates caused by a polymerization catalyser remainder was reduced as much as possible. On the surface of this polyester film, an intermediate layer was formed such that steep mountain-form projections were present in $1 \times 10^7$ pieces per 1 $mm^2$ comprising a silica colloid grain with an average diameter of 15 nm (150 angstroms) as a nucleus and an ultraviolet ray hardening epoxy resin as a bonding agent. The thickness of the intermediate layer was about 15 nm. Then, on top of this non-magnetic supporting material, a Co—Ni ferromagnetic film 2 (Ni content: 20 atm %, film thickness: 100 nm (1000 angstroms)) was disposed by using a consecutive vacuum diagonal evaporation method under a condition of minor oxygen. An oxygen content in the ferromagnetic film was 5% in an atomic fraction.

Furthermore, on top of the above-mentioned ferromagnetic film, a fluorine-containing carboxylic acid amine salt shown in Formula 5 was applied in an amount of 10 mg per 1 $m^2$ to form a lubricant layer 3. After that, it was cut at a predetermined width into a magnetic tape A. In addition, a 50 angstrom thick protection film made of a diamond-like carbon was formed by a plasma CVD method on top of this ferromagnetic film to produce a magnetic tape B in the same manner as magnetic tape A.

This magnetic tape had beem stored one week under the condition of 40° C. and 90% RH, and then, by using an X-ray light electron spectroscopic analysis (ESCA), the magnetic layer surface was examined before and after storage to see how high the fluorine residual was. In addition, the output property at steel reproduction was measured by applying the magnetic tape to a video cassette recorder under the conditions of 23° C. and 10% RH, and 40° C. and 80% RH. The steel endurance time was measured in which either the RF output decreased 3 dB against the initial value or until an output fluctuation occurred.

EXAMPLE 4

The same test was conducted by using magnetic tape B of Example 3 in which Formula 8 was applied to produce the magnetic tape in place of the compound of Formula 5.

EXAMPLE 5

The same test was conducted by using magnetic tape A of Example 3 in which the magnetic tape was produced by applying a mixed compound made of Formula 5 and a conventional well-known anticorrosive agent $C_8F_{17}C_2H_4NHC_{18}H_{35}$ at 2:1 weight ratio instead of the compound of Formula 5.

EXAMPLE 6

The same test was conducted by using magnetic tape B of Example 3 in which the magnetic tape was produced by applying a mixed compound made of Formula 5 and a conventional well-known lubricant agent $C_{17}H_{33}COOC_2H_4C_6F_{13}$ at 1:1 weight ratio 1:1 instead of the compound of Formula 5.

The results of the tests conducted in the embodiments mentiioned above are shown in Table 1. In this Table, lubricants used for the comparison samples 1, 2, and 3 correspond to Formula 1, 2, and 3 respectively discussed above.

TABLE 1

| Magnetic tape | Tape group | Fluorine residual (%) | Steel endurance time after storage test (min.) | |
|---|---|---|---|---|
| | | | 23° C., 10% RH | 40° C., 80% RH |
| Comparison 1 | B | 25 | 8 | 20 |
| Comparison 2 | A | 30 | 15 | 35 |
| Comparison 3 | B | 26 | 12 | 28 |
| Example 3 | A | 93 | 120 or more | 120 or more |
| Example 4 | B | 89 | 120 or more | 120 or more |
| Example 5 | A | 86 | 120 or more | 120 or more |
| Example 6 | B | 79 | 120 or more | 120 or more |

According to Table 1, it is clear that all the magnetic tapes disposed with a lubricant layer containing one or more kinds of the fluorine-containing carboxylic acid amine salt of this invention have excellent lubricity even after being stored in conditions of high temperature and high humidity. On the other hand, it is clear with the magnetic tapes disposed with a lubricant layer made solely of conventional lubricants that the amount of lubricants decreased when stored in conditions of high temperature and high humidity so that the lubricity deteriorated.

Furthermore, the above embodiments employed compounds of Formula 5, Formula 8, a mixed compound of Formula 5 and a conventional well-known lubricant, and a mixed compound of Formula 5 and an anticorrosive agent. However, the same effect can be attained by applying materials of Formula 11, Formula 12, Formula 13, Formula 14, and mixed compounds of these materials with conventional well-known lubricants and anticorrosive agents.

(Formula 11)

(Formula 12)

(Formula 13)

(Formula 14)

(Formula 15)

EXAMPLE 7

Next, a seventh embodiment of this invention is specifically described in the following.

A material of this embodiment is shown in Formula 16:

(Formula 16)

(molecular weight 1,754)

The material in Formula 16 is within the scope of Formula 4 where $R^1$ designates an aliphatic alkyl group with 18 carbons; $R^2$, a fluoroalkyl group with 8 carbons bonded to fluorine; $R^3$, a saturated hydrocarbon chain with 2 carbons; $R^4$, a saturated hydrocarbon chain with 3 carbons; $R^5$, a fluoroalkyl group with 8 carbons bonded to fluorine; and n, a second class amine salt.

The manufacturing method of the material shown in Formula 16 is explained hereafter.

The starting material is an amine with a fluoroalkyl group shown in Formula 17 and a material shown in Formula 18. The material shown in Formula 18 is a composite of octadesenyl succinic anhydride and 2-(perfluoro-n-octyl) ethanol.

(Formula 17)

(Formula 18)

81.7 g (0.10 mol) of the material shown in Formula 18 and 1000 ml of ethyl acetate were extracted into a 2-liter-flask with mixing wings, cooled to a temperature of 15° C., and dripped with 93.7 g (0.10 mol) of the material shown in Formula 17 which was dissolved in 400 ml of ethyl acetate. When the dripping was over, the reactive solution was put back at room temperature and was stirred continuously for two hours. After the reaction took place, 170 g of hyaline liquid was obtained as in Examples 1 and 2. This hyaline liquid was analysed by IR, GPC and FD-MS and was identified as a fluorine-containing carboxylic acid amine salt shown in Formula 16 which contained neither the starting material nor a by-product.

Figure 5:
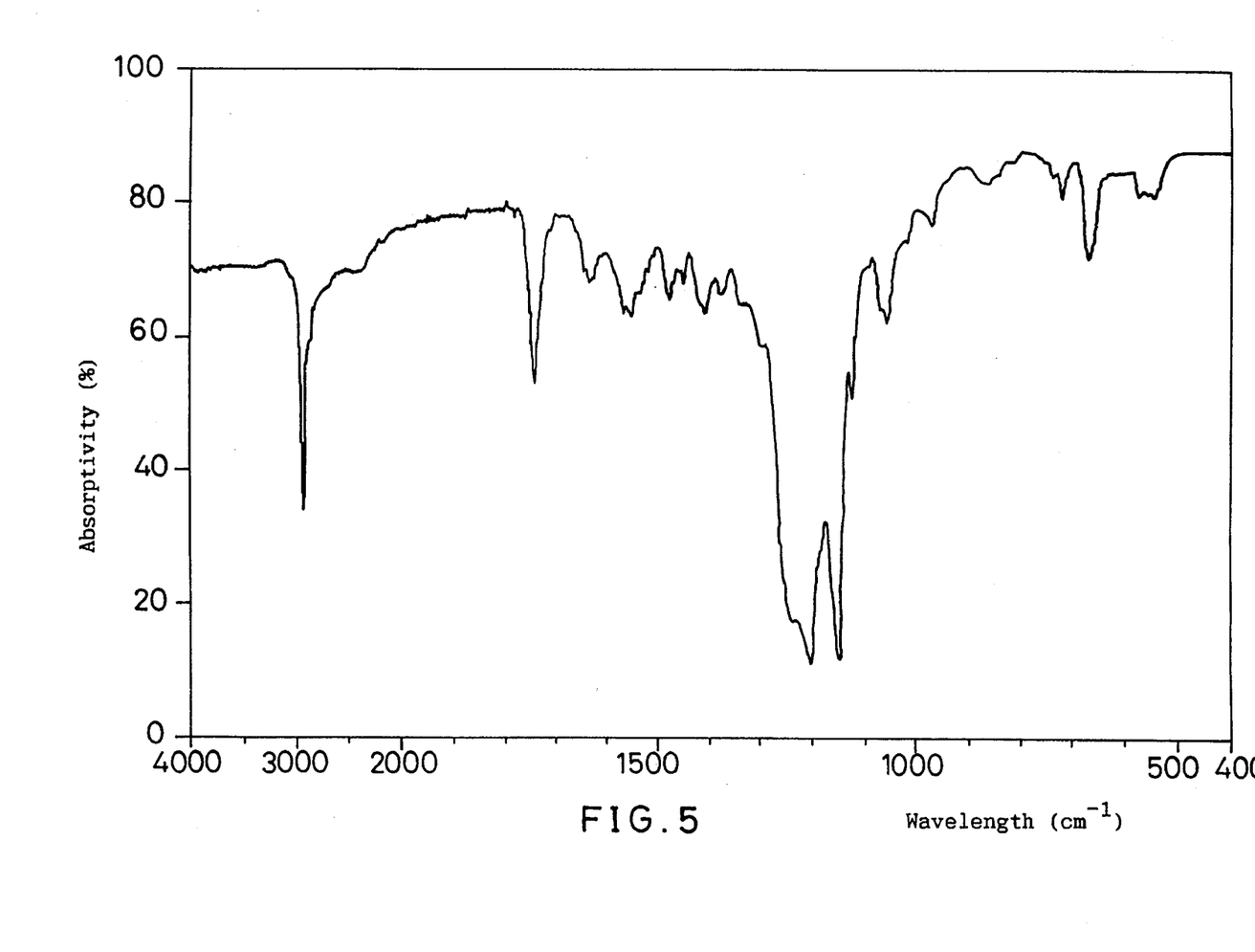
FIG. 5 is an infrared ray (IR) spectral chart of a seventh embodiment of this invention.

IR; an absorption peak of carboxylic acid disappeared at 1,705 cm$^{-1}$, an absorbtion peak of carboxylic acid amine salt appeared at 1540 cm$^{-1}$ (FIG. 5).

GPC; the starting material and a by-product were not detected.

FD-MS; m/e a main peak was present at 1,754.

As described above, according to the fluorine-containing carboxylic acid amine salt of this invention comprising two fluorine-containing hydrocarbon end groups within the same molecule, i.e., fluoroalkyl end groups, fluoroalkenyl end groups, fluorophenyl end groups or fluoroalkylether end groups, one aliphatic hydrocarbon end group, i.e., an aliphatic alkyl end group or an aliphatic alkenyl end group, and an amine carboxyl group, it is clear that it is effective in maintaining the lubricity even after being stored in conditions of high temperature and high humidity.

The invention may be embodied in other forms without departing from the spirit or essential characteristics thereof. The embodiments disclosed in this application are to be considered in all respects as illustrative and not restrictive, the scope of the invention is indicated by the appended claims rather than by the foregoing description, and all changes which come within the meaning and range of equivalency of the claims are intended to be embraced therein.

What is claimed is:

1. A fluorine-containing carboxylic acid amine salt of the following Formula 4,

(Formula 4)

wherein $R^1$ denotes an aliphatic alkyl group with 6 to 30 carbons or an aliphatic alkenyl group with 6 to 30 carbons; $R^2$ denotes a group selected from the group consisting of a fluoroalkyl group with 3 to 30 carbons, a fluoroalkenyl group with 3 to 30 carbons, a fluorophenyl group with 6 to 18 carbons, and a fluoroalkylether group with 5 to 50 carbons; $R^3$ and $R^4$ each independently denotes a saturated or unsaturated hydrocarbon chain with 1 to 20 carbons; $R^5$ denotes either a fluoroalkyl group with 3 to 30 carbons or a fluoroalkenyl group with 3 to 30 carbons; n denotes 0 or 1; X denotes hydrogen or -($R^6$)-$R^7$; and Y denotes hydrogen or -($R^8$)-$R^9$, where $R^6$ and $R^8$ each independently denotes a saturated or unsaturated hydrocarbon chain with 1 to 20 carbons, and $R^7$ and $R^9$ each independently denotes a fluoroalkyl group with 3 to 30 carbons or a fluoroalkenyl group with 3 to 30 carbons.

2. The fluorine-containing carboxylic acid amine salt as claimed in claim 1, wherein $R^1$ denotes an aliphatic alkyl group or an aliphatic alkenyl group with 10 to 24 carbons;

$R^2$ denotes a group selected from the group consisting of a fluoroalkyl group with 6 to 18 carbons, a fluoroalkenyl group with 3 to 30 carbons, a fluorophenyl group with 6 to 12 carbons, and a fluoroalkylether group with 5 to 30 carbons; $R^3$ and $R^4$ each independently represents a saturated or unsaturated hydrocarbon chain with 1 to 10 carbons; $R^5$ denotes either a fluoroalkyl group with 6 to 18 carbons or a fluoroalkenyl group with 6 to 18 carbons; $R^6$ and $R^8$ each independently denotes a saturated or unsaturated hydrocarbon chain with 1 to 10 carbons; and $R^7$ and $R^9$ each independently denotes a fluoroalkyl group with 6 to 18 carbons or a fluoroalkenyl group with 6 to 18 carbons.

3. A magnetic recording medium comprising a base material film disposed thereon with a ferromagnetic film and a lubricant layer disposed either directly or via a protection film on top of said ferromagnetic film, wherein said lubricant layer comprises one or more fluorine-containing carboxylic acid amine salt of Formula 4, (Formula 4)

wherein $R^1$ denotes an aliphatic alkyl group with 6 to 30 carbons or an aliphatic alkenyl group with 6 to 30 carbons; $R^2$ denotes a group selected from the group consisting of a fluoroalkyl group with 3 to 30 carbons, a fluoroalkenyl group with 3 to 30 carbons, a fluorophenyl group with 6 to 18 carbons, and a fluoroalkylether group with 5 to 50 carbons; $R^3$ and $R^4$ each denotes a saturated or unsaturated hydrocarbon chain with 1 to 20 carbons; $R^5$ denotes either a fluoroalkyl group with 3 to 30 carbons or a fluoroalkenyl group with 3 to 30 carbons; n denotes 0 or 1; X denotes hydrogen or $-(R^6)-R^7$; and Y denotes hydrogen or $-(R^8)-R^9$, where $R^6$ and $R^8$ each denotes a saturated or unsaturated hydrocarbon chain with 1 to 20 carbons, and $R^7$ and $R^9$ each denotes a fluoroalkyl group with 3 to 30 carbons or a fluoroalkenyl group with 3 to 30 carbons.

4. The magnetic recording medium as in claim 3, wherein a lubricant contained in said lubricant layer in present is an amount of from 0.05 to 100 mg per 1 $m^2$ film surface.

5. The magnetic recording medium as in claim 3, wherein said lubricant contained in the lubricant layer comprises the fluorine-containing carboxylic acid amine salt of Formula 4 at 90 weight percent or more.

6. The magnetic recording medium as in claim 5, wherein said lubricant contained in the lubricant layer comprises 50 weight percent or more of fluorine-containing carboxylic acid amine salt of Formula 4 and lubricant and anticorrosive agents made of other fluorine-containing compounds.

7. The magnetic recording medium as in claim 6, wherein said other fluorine-containing compounds are liquid fluorine-containing compounds.

8. The magnetic recording medium as in claim 3, wherein said protection film is present and has a thickness of from 5 to 50 nm and is at least one film selected from the group consisting of an amorphous-form carbon thin film, a graphite-form carbon thin film, a diamond-form carbon thin film, a mixed-form carbon thin film thereof, and a laminated-form carbon thin film thereof.

9. The magnetic recording medium as in claim 3, wherein said base material film has a thickness of from 3 to 30 μm and is at least one film selected from the group consisting of polyethylene terephthalate, polyethylene 2,6-naphthalate, and polyimide.

10. The magnetic recording medium as in claim 3, wherein said ferromagnetic film is a Co—Ni—O alloyed oxide film.

11. The magnetic recording medium as in claim 3, wherein a backing layer is disposed on said base material film on the side opposite the ferromagnetic film.

12. The magnetic recording medium as in claim 11, wherein said backing layer is a compound containing a binder resin and a filler material.

13. The magnetic recording medium as in claim 12, wherein said binder resin is at least one resin selected from the group consisting of polyester elastomer and cellulose nitrate, and said filler material is at least one material selected from the group consisting of calcium carbonate and carbon black.

* * * * *